United States Patent
Mailhe et al.

(10) Patent No.: US 9,858,689 B1
(45) Date of Patent: Jan. 2, 2018

(54) FAST AND MEMORY EFFICIENT REDUNDANT WAVELET REGULARIZATION WITH SEQUENTIAL CYCLE SPINNING

(71) Applicant: Siemens Healthcare GmbH, Erlangen (DE)

(72) Inventors: Boris Mailhe, Plainsboro, NJ (US); Alexander Ruppel, Alsenz (DE); Qiu Wang, Princeton, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/266,425

(22) Filed: Sep. 15, 2016

(51) Int. Cl.
  *G06T 11/00* (2006.01)
  *G06T 7/00* (2017.01)

(52) U.S. Cl.
  CPC ......... *G06T 11/005* (2013.01); *G06T 7/0012* (2013.01); *G06T 2207/10088* (2013.01); *G06T 2210/41* (2013.01); *G06T 2211/424* (2013.01)

(58) Field of Classification Search
  CPC ............ G01R 33/5611; G01R 33/5608; G01R 33/561; G01R 33/56; G01R 33/3415; G01R 33/4818; G01R 33/4835; A61B 5/055; A61B 5/7253; A61B 5/726; A61B 2576/00; G06T 11/003–11/008; G06T 2207/10088; G06T 2207/20048; G06F 17/141; G06F 17/142; G06F 17/148; G06F 17/30814
  USPC ................................................. 382/128–140
  See application file for complete search history.

(56) References Cited

U.S. PATENT DOCUMENTS

| | | | | |
|---|---|---|---|---|
| 8,014,616 | B2 * | 9/2011 | Chakraborty ......... | G06T 11/006 382/233 |
| 8,310,233 | B2 * | 11/2012 | Trzasko ............... | G01R 33/561 324/307 |
| 8,823,374 | B2 * | 9/2014 | Weller ............... | G01R 33/5611 324/307 |

(Continued)

OTHER PUBLICATIONS

Beck Amir, and Marc Teboulle. "A fast iterative shrinkage-thresholding algorithm for linear inverse problems." SIAM journal on imaging sciences 2.1 (2009): 183-202.
Bertsekas, Dimitri P. "Incremental proximal methods for large scale convex optimization." Mathematical programming 129.2 (2011): 163-195.

(Continued)

*Primary Examiner* — Michael Osinski

(57) ABSTRACT

A computer-implemented method of performing image reconstruction with sequential cycle-spinning includes a computer system acquiring an input signal comprising k-space data using a magnetic resonance imaging (MRI) device and initializing an estimate of a sparse signal associated with the input signal. The computer system selects one or more orthogonal wavelet transforms corresponding to a wavelet family and performs an iterative reconstruction process to update the estimate of the sparse signal over a plurality of iterations. During each iteration, one or more orthogonal wavelet transforms are applied to the estimate of the sparse signal to yield one or more orthogonal domain signals, the estimate of the sparse signal is updated by applying a non-convex shrinkage function to the one or more orthogonal domain signals, and a shift to the orthogonal wavelet transforms. Following the iterative reconstruction process, the computer system generates an image based on the estimate of the sparse signal.

20 Claims, 6 Drawing Sheets

(56) References Cited

U.S. PATENT DOCUMENTS

| | | | | |
|---|---|---|---|---|
| 8,948,480 | B2* | 2/2015 | Liu | G06T 11/005 382/128 |
| 9,229,080 | B2* | 1/2016 | Lin | G01R 33/56 |
| 9,466,102 | B2* | 10/2016 | Nadar | G06T 7/0012 |
| 9,507,003 | B2* | 11/2016 | Edelman | G01R 33/5635 |
| 9,542,761 | B2* | 1/2017 | Tan | G06T 11/003 |
| 9,760,536 | B2* | 9/2017 | Karakonstantis | G06F 17/142 |
| 2004/0101200 | A1* | 5/2004 | Peele | G06F 17/30814 382/218 |
| 2007/0110290 | A1* | 5/2007 | Chang | G06T 5/001 382/128 |
| 2009/0141995 | A1* | 6/2009 | Chakraborty | G01R 33/561 382/248 |
| 2010/0207629 | A1* | 8/2010 | Trzasko | G01R 33/561 324/309 |
| 2010/0308824 | A1* | 12/2010 | Grady | G01R 33/5611 324/309 |
| 2011/0215805 | A1* | 9/2011 | Doyle | G01R 33/4835 324/309 |
| 2012/0155730 | A1* | 6/2012 | Metaxas | G01R 33/5608 382/131 |
| 2013/0121554 | A1* | 5/2013 | Liu | G06T 11/005 382/131 |
| 2013/0310678 | A1* | 11/2013 | Balbi | A61B 5/055 600/410 |
| 2014/0086469 | A1* | 3/2014 | Lefebvre | G01R 33/5611 382/131 |
| 2014/0119626 | A1* | 5/2014 | Lin | G01R 33/445 382/131 |
| 2014/0197835 | A1* | 7/2014 | Kamada | G01R 33/4824 324/309 |
| 2015/0241534 | A1* | 8/2015 | Park | G01R 33/5611 382/131 |
| 2016/0187446 | A1* | 6/2016 | Zhou | G01R 33/5611 324/309 |
| 2016/0202336 | A1* | 7/2016 | Liang | G01R 33/485 324/309 |
| 2016/0306019 | A1* | 10/2016 | Wang | G01R 33/5611 |
| 2017/0035364 | A1* | 2/2017 | Noguchi | A61B 5/055 |
| 2017/0045598 | A1* | 2/2017 | Takeshima | G01R 33/4818 |
| 2017/0103529 | A1* | 4/2017 | Shi | G06T 7/0012 |
| 2017/0168129 | A1* | 6/2017 | Chen | G01R 33/56308 |
| 2017/0169563 | A1* | 6/2017 | Liang | G06T 7/0012 |
| 2017/0178318 | A1* | 6/2017 | Wang | G06T 7/0012 |

OTHER PUBLICATIONS

Candes, Emmanuel J., Michael B. Wakin, and Stephen P. Boyd. "Enhancing sparsity by reweighted $\ell$ 1 minimization." Journal of Fourier analysis and applications 14.5-6 (2008): 877-905.

Coifman, Ronald R., and David L. Donoho. Translation-invariant de-noising. Springer New York, 1995.

Combettes, Patrick L., and Jean-Christophe Pesquet. "Proximal splitting methods in signal processing." arXiv preprint 3rXiv:0912.3522 (2009).

Daubechies, Ingrid, Michel Defrise, and Christine De Mol. "An iterative thresholding algorithm for linear inverse problems with a sparsity constraint." Communications on pure and applied mathematics 57.11 (2004): 1413-1457.

Figueiredo, Mário AT, and Robert D. Nowak. "An EM algorithm for wavelet-based image restoration." IEEE Transactions on Image Processing 12.8 (2003): 906-916.

Gao, Hong-Ye. "Wavelet shrinkage denoising using the non-negative garrote." Journal of Computational and Graphical Statistics 7.4 (1998): 469-488.

Gao, Hong-Ye, and Andrew G. Bruce. "WaveShrink with firm shrinkage." Statistica Sinica (1997): 855-874.

Hunter, David R., and Kenneth Lange. "A tutorial on MM algorithms." The American Statistician 58.1 (2004): 30-37.

Kamilov, Ulugbek S., Emrah Bostan, and Michael Unser. "Variational justification of cycle spinning for wavelet-based solutions of inverse problems." IEEE Signal Processing Letters 21.11 (2014): 1326-1330.

Kowalski, Matthieu. "Thresholding rules and iterative shrinkage/thresholding algorithm: A convergence study." 2014 IEEE International Conference on Image Processing (ICIP). IEEE, 2014.

O'Donoghue, Brendan, and Emmanuel Candes. "Adaptive restart for accelerated gradient schemes." Foundations of computational mathematics 15.3 (2015): 715-732.

N. Parikh and S. Boyd. "Proximal Algorithms". In: Foundations and Trends in Optimization, vol. 1, No. 3 (2013), pp. 123-231.

San Emeterio, J. L., and Miguel A. Rodriguez-Hernandez. "Wavelet cycle spinning denoising of NDE ultrasonic signals using a random selection of shifts." Journal of Nondestructive Evaluation 34.1 (2015): 1-8.

Selesnick, Ivan. "Penalty and shrinkage functions for sparse signal processing." Connexions (2012), pp. 1-26.

Noodworth, Joseph, and Rick Chartrand. "Compressed sensing recovery via nonconvex shrinkage penalties." Inverse Problems 32.7 (2016): 075004.

\* cited by examiner

Input: $A, A^T, y, k = 0, \tau_0 = 1, x_0, z_0 = x_0, \lambda$
1: while $k < K$ do
2: $\quad \tau_{k+1} = \frac{1}{2}\left(1 + \sqrt{1 + 4\tau_k^2}\right)$
3: $\quad v_k = z_k - A^T A z_k + A^T y$
4: $\quad x_{k+1} = W_m^T \mathcal{T}(W_m v_k, \lambda)$
5: $\quad z_{k+1} = x_{k+1} + \left(\frac{\tau_k - 1}{\tau_{k+1}}\right)(x_{k+1} - x_k)$
6: $\quad m = 1 + (k - 1 \bmod M)$
7: $\quad k = k + 1$
8: end while

Input: $A, A^T, y, k=0, \tau_0=1, x_0, z_0=x_0, \lambda, W_1 \ldots W_N, \eta_1 \ldots \eta_N$ with $\sum \eta = 1$ 1: while $k < K$ do
2:    $\tau_{k+1} = \frac{1}{2}\left(1 + \sqrt{1 + 4\tau_k^2}\right)$
3:    $v_k = z_k - A^T A z_k + A^T y$
4:    $x_{k+1} = 0$
5:    for $n = 1 \to N$ do
6:      $w = W_{n,m}^T \mathcal{T}(W_{n,m} x_t, \lambda)$
7:      $x_{k+1} = x_{k+1} + \eta_n w$
8:    end for
9:    $z_{k+1} = x_{k+1} + \left(\frac{\tau_k - 1}{\tau_{k+1}}\right)(x_{k+1} - x_k)$
10:   $m = 1 + (k - 1 \mod M)$
11:   $k = k + 1$
12: end while

*FIG. 3*

Input: $A, A^T, y, k = 0, t = 0, \tau_0 = 1, x_0, z_0 = x_0, W_1 \ldots W_N, \eta_1 \ldots \eta_N$ with $\sum \eta = 1$ 1: while $k < K$ do
2:     $\tau_{k+1} = \frac{1}{2}\left(1 + \sqrt{1 + 4\tau_k^2}\right)$
3:     $v_k = z_k - A^T A z_k + A^T y$
4:     $x_t = v_k$
5:     while $t < T$ do
6:       $\alpha = 1/\sqrt{t}$
7:       $x_t = x_t - \alpha(x_t - v_k)$
8:       $x_{t+1} = 0$
9:       for $n = 1 \to N$ do
10:         $w = W_{n,m}^T \mathcal{T}(W_{n,m} x_t, \alpha \lambda)$
11:         $x_{t+1} = x_{t+1} + \eta_n w$
12:       end for
13:       $m = 1 + (t - 1 \mod M)$
14:       $t = t + 1$
15:     end while
16:     $x_{k+1} = x_{t+1}$
17:     $z_{k+1} = x_{k+1} + \left(\frac{\tau_k - 1}{\tau_{k+1}}\right)(x_{k+1} - x_k)$
18:     $k = k + 1$
19: end while

*FIG. 5*

FAST AND MEMORY EFFICIENT REDUNDANT WAVELET REGULARIZATION WITH SEQUENTIAL CYCLE SPINNING

TECHNOLOGY FIELD

The present invention relates generally to methods, systems, and apparatuses for Magnetic Resonance Imaging (MRI) reconstruction using wavelet regularization with sequential cycle spinning. The disclosed methods, systems, and apparatuses may be applied to various compressed-sensing MRI applications.

BACKGROUND

Imaging inverse problems such as reconstruction, deblurring, super-resolution, inpainting, or denoising can be solved by assuming the target image is sparse in the wavelet domain. Orthogonal wavelet transforms are not shift-invariant; image features are processed differently depending on their position with respect to the wavelet grid, and this can result in blocking artifacts.

An early way to reduce blocking artifacts in image denoising was the use of parallel cycle spinning: process the image separately with a wavelet transform offset by multiple different shifts in all dimensions, then average the results. However this simple averaging is not justified mathematically and makes the method difficult to extend to other inverse problems. As a result additional techniques have been developed such as the utilization of undecimated redundant wavelet transforms in conjunction with a nested inner algorithm inside the main solver (e.g. Chambolle-Pock or Dykstra inside FISTA) to solve the proximal operation performed during reconstruction.

These conventional methods require the application of multiple shifted wavelet transforms at each iteration, which incurs an extra computational cost of at least a factor of 2 per image dimension. Additionally, exact undecimated wavelet methods also require storing the wavelet coefficients of the image, which again are larger than the image by a factor of 2 in every dimension. This becomes too large with large-dimension use-cases such as dynamic volumetric reconstruction (3D+T), motion-compensated imaging, multi-contrast imaging including flow or diffusion, etc. Accordingly, it is desired to produce a reconstruction technique which minimizes blocking artifacts while also being efficient from a memory and computational standpoint.

SUMMARY

Embodiments of the present invention address and overcome one or more of the above shortcomings and drawbacks, by providing methods, systems, and apparatuses related to iteratively reconstructing MRI data using sequential cycle spinning (SCS). Briefly, SCS minimizes processing by applying only a single orthogonal wavelet transform at each iteration. This is done by separating the regularization into multiple terms corresponding to each possible shift of an orthogonal transform and then thresholding only one shift at a time.

According to some embodiments, a computer-implemented method of performing image reconstruction with sequential cycle-spinning includes a computer system acquiring an input signal comprising k-space data using a magnetic resonance imaging (MRI) device and initializing an estimate of a sparse signal associated with the input signal. The computer system selects one or more orthogonal wavelet transforms corresponding to a wavelet family and performs an iterative reconstruction process to update the estimate of the sparse signal over a plurality of iterations. During each iteration, one or more orthogonal wavelet transforms are applied to the estimate of the sparse signal to yield one or more orthogonal domain signals, the estimate of the sparse signal is updated by applying a non-convex shrinkage function (e.g., a soft-shrinkage function or non-negative garrote) to the one or more orthogonal domain signals, and a shift to the orthogonal wavelet transforms. This shift may be, for example, a circular, random, or diagonal shift. Following the iterative reconstruction process, the computer system generates an image based on the estimate of the sparse signal.

In some embodiments of the aforementioned method, the orthogonal wavelet transforms applied during each iteration comprise a plurality of different wavelet transforms and the estimate of the sparse signal is updated during each iteration by applying the non-convex shrinkage function to each orthogonal domain signal to calculate a plurality of signal estimates; and updating the estimate of the sparse signal with a weighted average of the plurality of signal estimates. In some embodiments, the different wavelet transforms of the estimate of the sparse signal are calculated in parallel across a plurality of processors. Additionally, the non-convex shrinkage function may be applied to each orthogonal domain signal in parallel across the plurality of processors.

In some embodiments of the aforementioned method, the wavelet family of the one or more orthogonal wavelet transforms is varied for each iteration of the iterative reconstruction process. For example, in one embodiment, the wavelet family is varied among a plurality of different wavelet families comprising a Haar wavelet family and a Daubechies wavelet family.

According to other embodiments, an article of manufacture for performing image reconstruction with sequential cycle-spinning includes a non-transitory, tangible computer-readable medium holding computer-executable instructions for performing the aforementioned method, with or without the additional features discussed above.

According to other embodiments, a system for performing image reconstruction with sequential cycle-spinning comprises an MRI device, a computer system, and a display. The MRI device comprises a plurality of coils configured to acquire an input signal comprising k-space data. The computer system is configured to initialize an estimate of a sparse signal associated with the input signal, select one or more orthogonal wavelet transforms corresponding to a wavelet family, and perform an iterative reconstruction process to update the estimate of the sparse signal over a plurality of iterations. During each iteration the orthogonal wavelet transforms are applied to the estimate of the sparse signal to yield one or more orthogonal domain signals, the estimate of the sparse signal is updated by applying a non-convex shrinkage function to the one or more orthogonal domain signals, and a shift is applied to the one or more orthogonal wavelet transforms. The display is configured to present an image generated based on the estimate of the sparse signal after the iterative reconstruction process.

In some embodiments of the aforementioned system, the orthogonal wavelet transforms applied during each iteration comprise a plurality of different wavelet transforms and the estimate of the sparse signal is updated during each iteration by applying the non-convex shrinkage function to each orthogonal domain signal to calculate a plurality of signal estimates; and updating the estimate of the sparse signal with a weighted average of the plurality of signal estimates. The computer system discussed above may include a plurality of processors and each of the plurality of different wavelet transforms of the estimate of the sparse signal may be calculated in parallel across the processors. Similarly, in some embodiments, the non-convex shrinkage function is applied to each orthogonal domain signal in parallel across the processors.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 3 provides an illustration of an alternative algorithm for performing FISTA with SCS, according to some embodiments;

FIG. 5 illustrates an algorithm that applies FISTA SCS with PW processing and a stochastic proximal, as may applied in some embodiments.

DETAILED DESCRIPTION OF ILLUSTRATIVE EMBODIMENTS

The following disclosure describes the present invention according to several embodiments directed at methods, systems, and apparatuses for performing Magnetic Resonance Imaging (MRI) reconstruction using wavelet regularization with sequential cycle spinning (SCS). The goal of SCS is to use the complete undecimated wavelet transform during iterative image reconstruction, but to minimize it by applying only a single orthogonal wavelet transform at each iteration. This is done by separating the regularization into multiple terms corresponding to each possible shift of an orthogonal transform, then thresholding only one shift at a time. The SCS loop itself converges when browsing through the shifts with a decreasing learning rate to avoid circling around the minimum. Moreover, SCS can also be used with non-convex thresholding functions such as p-shrinkage and shows empirical convergence. Processing orthogonal transforms separately also simplifies the implementation of multi-level transforms. SCS can also be employed to combine several different types of wavelets (e.g., Daubechies wavelets of different support length). The techniques described herein may be applied to many if not all compressed sensing use-cases to provide an overall performance improvement without sacrificing image quality.

Figure 1:
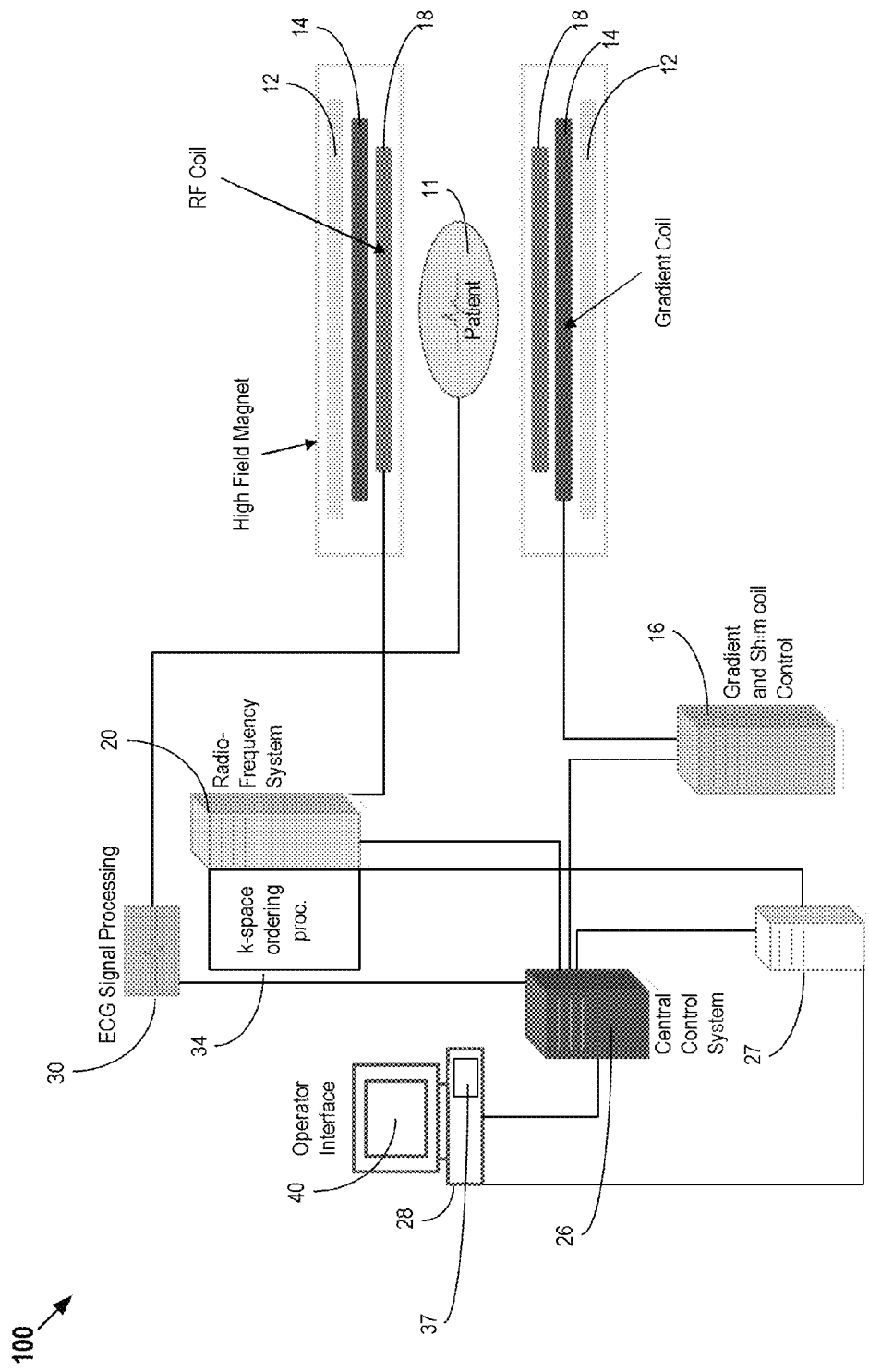
FIG. 1 shows a system for ordering acquisition of frequency domain components representing magnetic resonance (MR) image data for storage in a k-space storage array, as used by some embodiments of the present invention.

FIG. 1 shows a system 100 for ordering acquisition of frequency domain components representing Magnetic Resonance (MR) image data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and the magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for presentation on display 40, for example.

Many challenges in medical imaging such as reconstruction, denoising or super-resolution can be modeled mathematically as ill-posed linear inverse problems:

$$y = Ax + n \quad (1)$$

where the goal is to reconstruct an unknown signal y from partially incomplete data x that is corrupted by measurement noise n. The matrix A models the measurement system. In case of parallel MRI it is often modeled as A=FS with F representing the (partial) Fourier transform and S containing the coil sensitivities. Because the system is underdetermined, there exists infinitely many solutions to it and additional constrains to the solution must be imposed. A standard approach to the estimator of Equation (1) is as follows:

$$\hat{x} = \operatorname*{argmin}_{x} \frac{1}{2} \|y - Ax\|_2^2 + \lambda \Phi(x) \quad (2)$$

where $\frac{1}{2}\|y-Ax\|_2^2$ is the data fidelity term to enforce the solution to be close to the measurements and the function $\Phi(x)$ is called the regularizer with $\lambda > 0$ being the regularization parameter to balance the trade-off between the data fidelity and the regularization.

In many cases, we seek the solution to be sparse with respect to a given basis, meaning, having only few non-zero coefficients in that basis. A popular approach in compressed sensing is a wavelet based framework and promoting sparsity in a given wavelet basis such as Haar. However, having the measure of non-zeros $\|\cdot\|_0$ as a regularizer yields to a highly non-convex and intractable combinatorial problem, which is known to be NP-hard. Thus, in case of a wavelet based compressed sensing, the regularizer has often the form of $\|Wx\|_1$ and promotes sparsity with respect to the $l_1$-norm that is known to be a convex approximation to the $l_0$ pseudo-norm. Here W represents a wavelet transform. In general, W can be any linear operator depending on the underlying problem. For example, for MRI reconstruction, an undecimated wavelet transform is the preferable choice due to its translation invariance. However, the choice of algorithms to solve the optimization problem depends on the underlying regularizer. A popular and efficient algorithm to solve Equation (1) is the iterative shrinkage/thresholding algorithm (ISTA), which is a special case of so called forward-backward splitting algorithms. The idea is to split the problem into functions $$f_1 = \frac{1}{2}\|y - Ax\|_2^2 \text{ and } f_2 = \lambda \Phi(x)$$

and use them individually. Since $f_2$ is often non-smooth it is processed via its proximity operator. The iterative scheme is to take a gradient step on the function $f_1$ (forward step) and evaluate the proximity operator of function $f_2$ at that new point (backward step). Redundant wavelet transforms can be handled by using a Chambolle-Pock type algorithm for the proximal step. However, from a practical perspective, using orthogonal wavelets have the advantage of reducing the memory consumption and therefore faster processing times.

Given a function g(x), the proximal operator is the solution of the minimization problem:

$$\operatorname*{prox}_{\lambda_{ij}}(u) = \operatorname*{argmin}_{x} \lambda g(x) + \frac{1}{2}\|x - u\|_2^2. \quad (3)$$

Note that Equation (3) is essentially a denoising problem. Many functions have closed form solutions of their proximal operator. Of special interest in this work is the proximal operator of the $l_1$-norm, which yields the soft-shrinkage operator defined as the point-wise shrinkage function:

$$\mathcal{T}_{soft}(x,\lambda) = \max\{|x_i| - \lambda, 0\} \operatorname{sign}(x_i) \quad (4)$$

An efficient algorithm to solve Equation (2) that utilizes proximal operations is the iterative shrinkage/thresholding algorithm called ISTA and its accelerated version called Fast-ISTA (FISTA). In the following, the algorithm will be derived from the perspective of the majorization-minimization (MM) prescription. The idea behind MM is to minimize a convex surrogate to a function rather than the function itself. Consider a function $Q(\Theta|\Theta^m)$ of $\Theta$ that depends on a fixed parameter $\Theta^m$. Given a function $f(\Theta)$, $Q(\Theta|\Theta^m)$ is said to majorize $f$ at the point $\Theta^m$ if $$Q(\theta|\theta^m) \geq f(\theta) \text{ for all } \theta, \quad (5)$$

$$Q(\theta^m|\theta^m) = f(\theta^m) \quad (6)$$

The minimizer of the function Q can be shown to descent the function $f$ such that $$f(\theta^{m+1}) \leq f(\theta^m). \quad (7)$$

The minimization problem shown in Equation (2) can be split into two functions $$f(x) = \frac{1}{2}\|y - Ax\|_2^2 \text{ and } \Phi(x).$$

Incorporating this into the MM prescription, we can majorize $F:=f(x)+\Phi(x)$ by a first order approximation at a given point $x_k$ with:

$$Q(x|x_k) = f(x_k) + \nabla f(x_k)(x - x_k) + \frac{1}{2}\|x - x_k\|_2^2 + \lambda \Phi(x). \quad (8)$$

Q satisfies the conditions in Equations (5) and (6) for a given $x_k$ and with $\lambda \in (0, 1/L]$, where L is a Lipschitz constant of $\nabla f$ and $\Phi(x) \geq 0 \forall x$.

Iteratively minimizing Q yields the IST algorithm:

$$x_{k+1} = \arg\min_x Q(x \mid x_k) \quad (9)$$
$$= \arg\min_x \left\{ \lambda \Phi(x) + \frac{1}{2} \|x - (x_k - \nabla f(x_k))\|_2^2 \right\}.$$

It can easily be seen that Equation (9) admits the form of Equation (3) with $u = x_k - \nabla f(x_k)$ and thus, the IST algorithm can also be written as:

$$x_{k+1} = \text{prox}_{\lambda \Phi}(x_k - \nabla f(x_k)). \quad (10)$$

If $\Phi = 0$, Equation 10 comprises minimizing a smooth convex function and, thus, reduces to the simple gradient method. If $\Phi$ is the $l_1$-norm, $\text{prox}_{\lambda \Phi}$ yields the closed form solution given in Equation 4.

ISTA can be further adapted with an accelerated scheme referred to as Fast ISTA or simply FISTA. FISTA includes an extrapolating step in the algorithm:

$$x_{k+1} = \text{prox}_{\lambda \Phi}(z_k - \nabla f(z_k)) \quad (11)$$
$$\tau_{k+1} = \frac{1}{2}\left(1 + \sqrt{1 + 4\tau_k^2}\right)$$
$$z_{k+1} = x_k + \left(\frac{\tau_k - 1}{\tau_{k+1}}\right)(x_k - x_{k-1}).$$

where the initializers are $\tau_1 = 1$ and $y = x_0$. Additionally, FISTA may be further generalized in a form referred to as relaxed ISTA where the extrapolation step is expressed as:

$$z_{k+1} = x_k + \gamma_k (x_k - x_{k-1}), \quad (12)$$

and arbitrary $\gamma_k$.

The algorithms discussed above only apply if $\Phi(\cdot)$ is separable. However, in a wavelet based framework, one often encounters $\Phi(x) = \|Wx\|_1$. If W is an orthogonal transform, $\Phi(\cdot)$ is separable and the above schemes can be applied for finding sparse solutions. In practical settings however, orthogonal wavelet transforms perform rather poorly because of their lack of shift-invariance. In MRI reconstruction, this yields to more noise and block artifacts in the reconstructed image compared to undecimated wavelet transforms. On the other hand, undecimated or redundant transforms have the disadvantage of having higher memory consumption because of the missing decimation step.

The concept of making an orthogonal transform translation invariant was first introduced for wavelet denoising with the name cycle-spinning. The general idea behind cycle-spinning is to "average out" the translation dependence by circularly shifting the input signal, transforming into the orthogonal domain, applying thresholding/shrinking, and circularly shifting back the result. By repeating these steps for a range of shifts and averaging the results, a reconstruction may be produced with fewer artifacts compared to orthogonal transforms. The maximum number of shifts M can be computed by $M = 2^J$ with J being the maximum wavelet decomposition level in each dimension. For example, for a 3-dimensional dataset, a single decomposition level, and Daubechies-1 wavelet, a total of $M = 8$ shifts are required to make the transform shift-invariant.

One disadvantage of conventional wavelet cycle-spinning is that the transform has to be applied M times for each iteration. This slows down overall computation of the reconstruction algorithm. To address this computational inefficiency, the techniques described herein apply a sequential cycle-spinning algorithm where only one shift and transform is required per iteration. Shifts are then cycled through the outer FISTA loop. This results in faster reconstruction compared to conventional techniques, while providing similar image quality.

Figure 2:
FIG. 2 provides an illustration of an algorithm for performing FISTA with SCS, according to some embodiments.

FIG. 2 provides an illustration of an algorithm 200 for performing FISTA with SCS, according to some embodiments. Here, $W_m$ is the orthogonal wavelet transform with the m-th circular shift applied to the signal and $\mathcal{T}$ is a non-negative thresholding function (e.g., soft-thresholding). The algorithm 200 is performed for a predetermined number of iterations (denoted by K), which may be specified by the user based on, for example, a priori knowledge of standard values required to meet image quality goals. At line 2, the acceleration factor is calculated. Then, the gradient (forward) step and proximal (backward) step are performed at lines 3 and 4, respectively. This is followed at line 5 by the FISTA extrapolation. At line 6 the value of m is adjusted such that the proximal step will move to the next shift of orthogonal wavelet transform W. In the example of FIG. 2, a circular shift formula is utilized; however, in other embodiments, different shift formulas may alternatively be applied (e.g., random shifting, diagonal shifting, etc.). Finally, at line 7, the value of k is increased and the loop either continues to the next iteration or terminates if the value of K has been reached.

FIG. 3 provides an illustration of an alternative algorithm 300 for performing FISTA with SCS, according to some embodiments. This algorithm 300 extends the general concepts discussed above with respect to FIG. 2 by performing parallel wavelet (PW) processing. This is shown in lines 5-8 where the proximal step from algorithm 200 is replaced with a weighted average of N different orthogonal transforms. Here, the value of $W_{n,m}$ is one of N orthogonal wavelet transforms with the m-th circular shift applied to the signal. The weights (denoted by $\eta$) are predetermined to emphasize certain wavelets over others. In some embodiments, a static set of weights may be used which are based on, for example, experimental testing of the algorithm 300. In other embodiments, the weights may be determined at runtime by a step not shown in algorithm 300 based on characteristics of the input signal.

Figure 4:
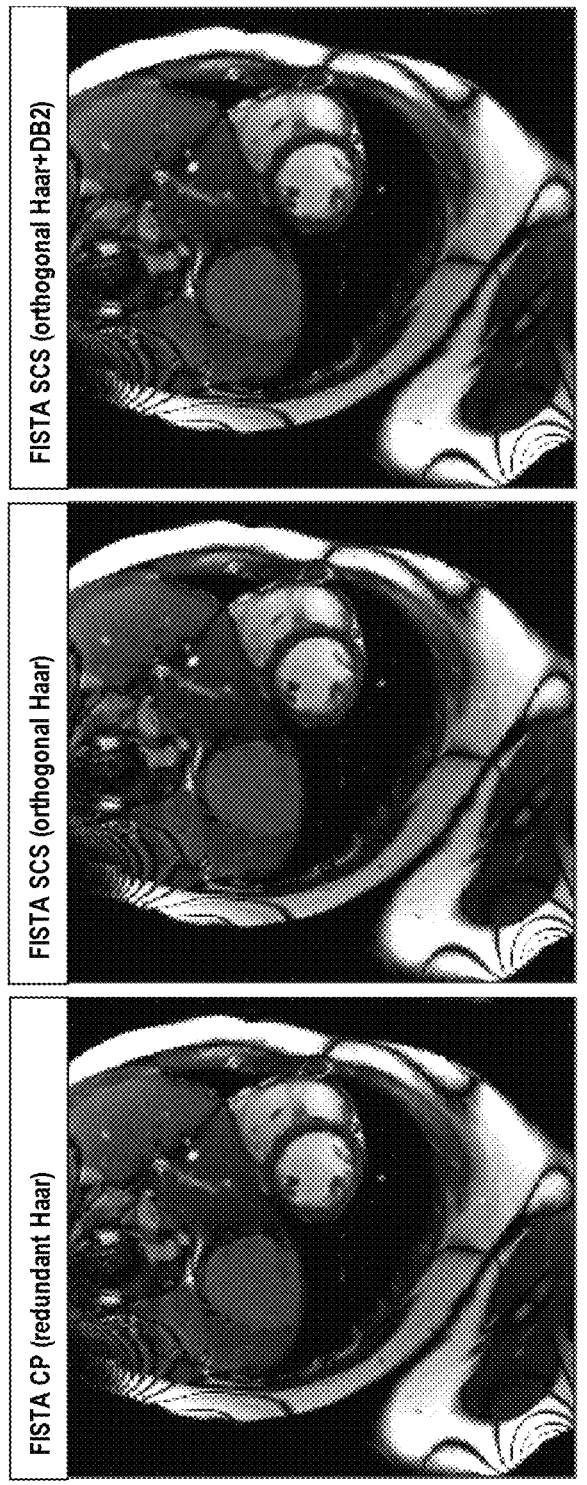
FIG. 4 provides a comparison of FISTA SCS with a conventional implementation of FISTA with Chambolle-Pock (CP) for the proximal step.

FIG. 4 provides a comparison of FISTA SCS with a conventional implementation of FISTA with Chambolle-Pock (CP) for the proximal step. As shown in this example, implementation of FISTA SCS with an orthogonal Haar wavelet provides a dramatic decrease in the overall reconstruction time while only sacrificing some of the image quality (as reflected by the decrease in the peak signal-to-noise, or PSNR). The rightmost image in FIG. 4 shows an implementation of FISTA SCS where the wavelet family is varied between iterations. Here a combination of orthogonal Haar and Daubechies 2 reconstructs the data in approximately half the time of the conventional case, while also providing an increase in PSNR.

General sparse recovery with a $l_0$-norm (i.e., number of non-zero elements) may be described by the following equation:

$$\arg\min_x \frac{1}{2} \|y - Ax\|_2^2 + \lambda \|x\|_0 \quad (13)$$

This is an NP-hard combinatorial problem. Thus, it is often approximated with the convex $l_1$-norm as follows:

$$\underset{x}{\mathrm{argmin}}\,\frac{1}{2}\|y-Ax\|_2^2+\lambda\|x\|_1 \quad (14)$$

Equation 14 is the form utilized by algorithms such as FISTA. However, the latest research in reconstruction suggests that the following equation with utilizing a non-convex $l_p$-norm (p<1) provides a better approximation of the $l_0$-norm:

$$\underset{x}{\mathrm{argmin}}\,\frac{1}{2}\|y-Ax\|_2^2+\lambda\|x\|_p \quad (15)$$

Optimization with Equation 15 provides better results than Equation 16 with fewer measurements. Additionally, where the same number of measurements is used, the $l_p$-norm offers better image quality than the $l_1$ optimization. Using a $l_p$-norm, the following generalized non-convex shrinkage function may be applied which applies a proximal mapping of a non-convex penalty:

$$\mathcal{T}_p(x,\lambda,p)=\max\{|x|-\lambda^{2-p}|x_i|^{p-1},0\}\mathrm{sign}(x) \quad (16)$$

Equation 16 reduces to soft-shrinkage for p=1 and non-negative garrote for p=0. It should be noted that larger values for p<1 are penalized. Accordingly, in some embodiments, Equation 16 may replace the soft-shrinkage operator in the algorithms 200, 300 shown in FIGS. 2 and 3, respectively.

FIG. 5 illustrates an algorithm 500 that applies FISTA SCS with PW processing and a stochastic proximal, as may applied in some embodiments. This algorithm is similar to the algorithm 300 shown in FIG. 3, however, algorithm 500 utilizes a diminishing proximal step-size (represented by a) while cycling through shifts within the proximal step. Thus, lines 4-8 of algorithm 300 are replaced with lines 4-16 in the algorithm 500 shown in FIG. 5. For T=1 algorithm 500 reduces to FISTA SCS PW (i.e., algorithm 300 shown in FIG. 3). Increasing T yields an incremental proximal algorithm that converges to a fixed point. With T=8 one can achieve similar convergence results as Chambolle-Pock. In practice, T=1 yields good results, but the optimization cycles around a fixed point rather than converging.

Figure 6:
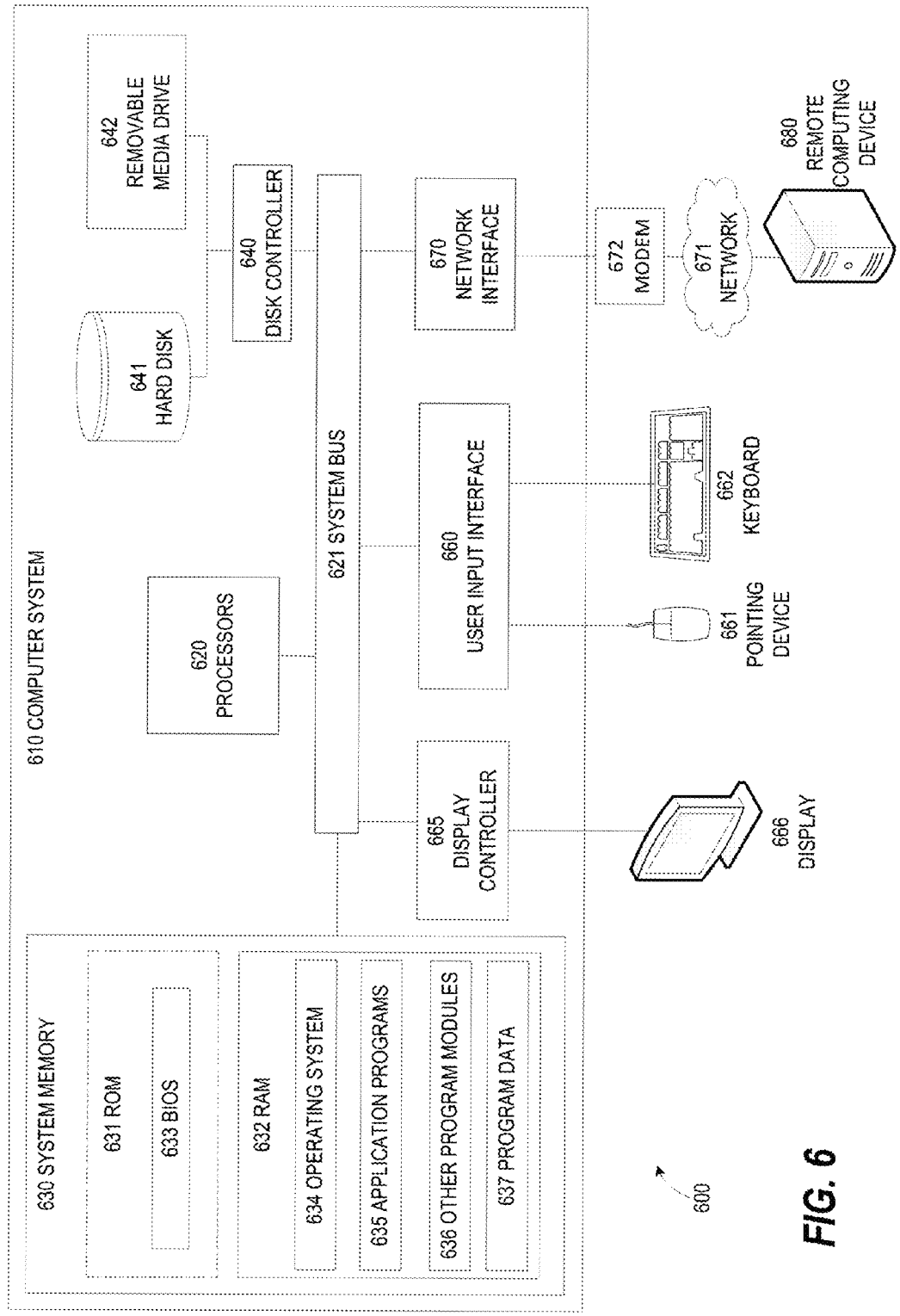
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be used to implement processes for the algorithms 200, 300, 500 shown in FIGS. 2, 3, and 5, respectively. In some embodiments, the computing environment 600 may be used to implement one or more of the components illustrated in the system 100 of FIG. 1. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system 633 (BIOS) containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT) or liquid crystal display (LCD), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hardwired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for.

We claim:
1. A computer-implemented method of performing image reconstruction with sequential cycle-spinning, the method comprising:
   acquiring, by a computer system, an input signal comprising k-space data using a magnetic resonance imaging (MRI) device;
   initializing, by the computer system, an estimate of a sparse signal associated with the input signal;

selecting, by the computer system, one or more orthogonal wavelet transforms corresponding to a wavelet family;
performing, by the computer system, an iterative reconstruction process to update the estimate of the sparse signal over a plurality of iterations, wherein each iteration comprises:
applying the one or more orthogonal wavelet transforms to the estimate of the sparse signal to yield one or more orthogonal domain signals,
updating the estimate of the sparse signal by applying a non-convex shrinkage function to the one or more orthogonal domain signals, and
applying a shift to the one or more orthogonal wavelet transforms; and
following the iterative reconstruction process, generating an image based on the estimate of the sparse signal.

2. The method of claim 1, wherein the one or more orthogonal wavelet transforms applied during each iteration comprise a plurality of different wavelet transforms and the estimate of the sparse signal is updated during each iteration by:
applying the non-convex shrinkage function to each orthogonal domain signal to calculate a plurality of signal estimates; and
updating the estimate of the sparse signal with a weighted average of the plurality of signal estimates.

3. The method of claim 2, wherein each of the plurality of different wavelet transforms of the estimate of the sparse signal is calculated in parallel across a plurality of processors.

4. The method of claim 3, wherein the non-convex shrinkage function is applied to each orthogonal domain signal in parallel across the plurality of processors.

5. The method of claim 1, wherein the shift of the one or more orthogonal wavelet transforms is a circular shift.

6. The method of claim 1, wherein the shift of the one or more orthogonal wavelet transforms is a random shift.

7. The method of claim 1, wherein the one or more orthogonal wavelet transforms are included in a matrix of orthogonal wavelet transforms and the shift is a diagonal shift.

8. The method of claim 1, wherein the wavelet family of the one or more orthogonal wavelet transforms is varied for each iteration of the iterative reconstruction process.

9. The method of claim 8, wherein the wavelet family is varied among a plurality of different wavelet families comprising a Haar wavelet family and a Daubechies wavelet family.

10. The method of claim 1, wherein the non-convex shrinkage function is a soft-shrinkage function.

11. The method of claim 1, wherein the non-convex shrinkage function is a non-negative garrote function.

12. An article of manufacture for performing image reconstruction with sequential cycle-spinning, the article of manufacture comprising a non-transitory, tangible computer-readable medium holding computer-executable instructions for performing a method comprising:
receiving an input signal comprising k-space data acquired using a magnetic resonance imaging (MRI) device;
initializing an estimate of a sparse signal associated with the input signal;
selecting one or more orthogonal wavelet transforms corresponding to a wavelet family;
performing an iterative reconstruction process to update the estimate of the sparse signal over a plurality of iterations, wherein each iteration comprises:
applying the one or more orthogonal wavelet transforms to the estimate of the sparse signal to yield one or more orthogonal domain signals,
updating the estimate of the sparse signal by applying a non-convex shrinkage function to the one or more orthogonal domain signals, and
applying a shift to the one or more orthogonal wavelet transforms; and
following the iterative reconstruction process, generating an image based on the estimate of the sparse signal.

13. The article of manufacture of claim 12, wherein the one or more orthogonal wavelet transforms applied during each iteration comprise a plurality of different wavelet transforms and the estimate of the sparse signal is updated during each iteration by:
applying the non-convex shrinkage function to each orthogonal domain signal to calculate a plurality of signal estimates; and
updating the estimate of the sparse signal with a weighted average of the plurality of signal estimates.

14. The article of manufacture of claim 12, wherein the shift of the one or more orthogonal wavelet transforms is a circular shift.

15. The article of manufacture of claim 12, wherein the shift of the one or more orthogonal wavelet transforms is a random shift.

16. The article of manufacture of claim 12, wherein the one or more orthogonal wavelet transforms are included in a matrix of orthogonal wavelet transforms and the shift is a diagonal shift.

17. A system for performing image reconstruction with sequential cycle-spinning, the system comprising:
a magnetic resonance imaging device comprising a plurality of coils configured to acquire an input signal comprising k-space data;
a computer system configured to:
initialize an estimate of a sparse signal associated with the input signal;
select one or more orthogonal wavelet transforms corresponding to a wavelet family;
perform an iterative reconstruction process to update the estimate of the sparse signal over a plurality of iterations, wherein each iteration comprises:
applying the one or more orthogonal wavelet transforms to the estimate of the sparse signal to yield one or more orthogonal domain signals,
updating the estimate of the sparse signal by applying a non-convex shrinkage function to the one or more orthogonal domain signals, and
applying a shift to the one or more orthogonal wavelet transforms; and
a display configured to present an image generated based on the estimate of the sparse signal after the iterative reconstruction process.

18. The system of claim 17, wherein the one or more orthogonal wavelet transforms applied during each iteration comprise a plurality of different wavelet transforms and the estimate of the sparse signal is updated during each iteration by:
applying the non-convex shrinkage function to each orthogonal domain signal to calculate a plurality of signal estimates; and
updating the estimate of the sparse signal with a weighted average of the plurality of signal estimates.

19. The system of claim 18, wherein the computer system comprises a plurality of processors and each of the plurality of different wavelet transforms of the estimate of the sparse signal are calculated in parallel across the plurality of processors.

20. The system of claim 19, wherein the non-convex shrinkage function is applied to each orthogonal domain signal in parallel across the plurality of processors.

* * * * *